(12) United States Patent
Hirschl

(10) Patent No.: US 9,283,086 B2
(45) Date of Patent: Mar. 15, 2016

(54) EXPANDABLE CORPECTOMY CAGE

(75) Inventor: Robert Alex Hirschl, Clive, IA (US)

(73) Assignee: Life Spine, Inc., Huntley, IL (US)

( * ) Notice: Subject to any disclaimer, the term of this patent is extended or adjusted under 35 U.S.C. 154(b) by 812 days.

(21) Appl. No.: 13/409,357

(22) Filed: Mar. 1, 2012

(65) Prior Publication Data
US 2012/0226356 A1  Sep. 6, 2012

Related U.S. Application Data

(60) Provisional application No. 61/448,981, filed on Mar. 3, 2011.

(51) Int. Cl.
*A61F 2/44* (2006.01)
*A61F 2/30* (2006.01)

(52) U.S. Cl.
CPC .............. *A61F 2/442* (2013.01); *A61F 2/4455* (2013.01); *A61F 2/30965* (2013.01); *A61F 2/447* (2013.01); *A61F 2/4465* (2013.01); *A61F 2002/3039* (2013.01); *A61F 2002/30235* (2013.01); *A61F 2002/30265* (2013.01); *A61F 2002/30271* (2013.01); *A61F 2002/30403* (2013.01); *A61F 2002/30433* (2013.01); *A61F 2002/30472* (2013.01); *A61F 2002/30522* (2013.01); *A61F 2002/30601* (2013.01); *A61F 2002/30607* (2013.01); *A61F 2002/30616* (2013.01); *A61F 2002/30779* (2013.01); *A61F 2002/30784* (2013.01); *A61F 2002/30785* (2013.01); *A61F 2002/30789* (2013.01); *A61F 2002/30948* (2013.01); *A61F 2002/448* (2013.01); *A61F 2002/449* (2013.01); *A61F 2002/4485* (2013.01); *A61F 2310/00419* (2013.01)

(58) Field of Classification Search
CPC ......... A61F 2/44; A61F 2/445; A61F 2/4465; A61F 2/4475; A61F 2002/30601; A61F 2002/3055
USPC ................................ 606/247–249, 250–263; 623/17.11–17.16
See application file for complete search history.

(56) References Cited

U.S. PATENT DOCUMENTS

| | | | |
|---|---|---|---|
| 5,059,193 A | 10/1991 | Kuslich | |
| 5,171,278 A | 12/1992 | Pisharodi | |
| 5,236,460 A * | 8/1993 | Barber | 623/17.15 |
| 5,290,312 A | 3/1994 | Kojimoto et al. | |
| 5,336,223 A * | 8/1994 | Rogers | 606/258 |
| 5,405,391 A * | 4/1995 | Hednerson et al. | 623/17.15 |
| 5,458,641 A * | 10/1995 | Ramirez Jimenez | 623/17.11 |
| 5,480,442 A * | 1/1996 | Bertagnoli | 623/17.14 |
| 5,514,180 A * | 5/1996 | Heggeness et al. | 623/17.16 |
| 5,702,453 A * | 12/1997 | Rabbe et al. | 623/17.16 |
| 5,723,013 A * | 3/1998 | Jeanson et al. | 623/17.16 |
| 6,066,175 A | 5/2000 | Henderson et al. | |
| 6,126,689 A | 10/2000 | Brett | |
| 6,176,881 B1 * | 1/2001 | Schar et al. | 623/17.11 |
| 6,176,882 B1 | 1/2001 | Biedermann et al. | |
| 6,193,756 B1 * | 2/2001 | Studer et al. | 623/17.15 |
| 6,200,348 B1 * | 3/2001 | Biedermann et al. | 623/17.11 |

(Continued)

*Primary Examiner* — Mary Hoffman
(74) *Attorney, Agent, or Firm* — Foley & Lardner LLP

(57) ABSTRACT

A corpectomy cage is provided with upper and lower telescoping members which move axially between extended and retracted positions. A fixed length sleeve fits over the telescoping members. The sleeve is load bearing to support axial loads on the cage from vertebral bodies. The sleeve also prevents the telescoping members from retracting and encloses an internal cavity within the cage for packing bone fusion material.

17 Claims, 15 Drawing Sheets

(56) References Cited

U.S. PATENT DOCUMENTS

| | | | |
|---|---|---|---|
| 6,375,683 B1* | 4/2002 | Crozet et al. | 623/17.15 |
| 6,648,891 B2 | 11/2003 | Kim | |
| 6,866,682 B1 | 3/2005 | An et al. | |
| 7,226,481 B2 | 6/2007 | Kuslich | |
| 7,393,361 B2* | 7/2008 | Zubok et al. | 623/17.15 |
| 7,458,988 B2 | 12/2008 | Trieu et al. | |
| 7,544,208 B1 | 6/2009 | Mueller et al. | |
| 7,628,800 B2 | 12/2009 | Sherman et al. | |
| 7,674,296 B2 | 3/2010 | Rhoda et al. | |
| 7,758,648 B2* | 7/2010 | Castleman et al. | 623/17.16 |
| 7,794,501 B2 | 9/2010 | Edie et al. | |
| 7,815,683 B2 | 10/2010 | Melkent et al. | |
| 7,824,445 B2 | 11/2010 | Biro et al. | |
| 7,909,870 B2* | 3/2011 | Kraus | 623/17.11 |
| 8,062,366 B2* | 11/2011 | Melkent | 623/17.11 |
| 8,187,331 B2* | 5/2012 | Strohkirch et al. | 623/17.16 |
| 8,252,054 B2* | 8/2012 | Greenhalgh et al. | 623/17.11 |
| 8,721,723 B2* | 5/2014 | Hansell et al. | 623/17.15 |
| 2001/0056302 A1* | 12/2001 | Boyer et al. | 623/17.15 |
| 2002/0161441 A1* | 10/2002 | Lang et al. | 623/17.11 |
| 2003/0083749 A1 | 5/2003 | Kuslich et al. | |
| 2003/0181980 A1* | 9/2003 | Berry et al. | 623/17.11 |
| 2003/0191531 A1* | 10/2003 | Berry et al. | 623/17.11 |
| 2003/0220643 A1* | 11/2003 | Ferree | 606/61 |
| 2004/0158250 A1 | 8/2004 | Chappuis | |
| 2005/0338501 | 10/2005 | Miller et al. | |
| 2006/0100710 A1* | 5/2006 | Gutlin et al. | 623/17.15 |
| 2007/0350171 | 10/2007 | Bonin, Jr. | |
| 2008/0046083 A1* | 2/2008 | Hewko | 623/17.16 |
| 2008/0058930 A1* | 3/2008 | Edie et al. | 623/17.11 |
| 2008/0288071 A1 | 11/2008 | Biyani et al. | |
| 2009/0118765 A1 | 5/2009 | Mueller et al. | |
| 2009/0138083 A1 | 5/2009 | Biyani | |
| 2009/0138089 A1 | 5/2009 | Doubler et al. | |
| 2009/0164018 A1 | 6/2009 | Sommerich et al. | |
| 2010/0030335 A1* | 2/2010 | Arramon | 623/17.13 |
| 2010/0179594 A1* | 7/2010 | Theofilos et al. | 606/247 |
| 2010/0179656 A1 | 7/2010 | Theofilos | |
| 2010/0280616 A1 | 11/2010 | Frasier | |
| 2013/0310938 A1* | 11/2013 | Sournac et al. | 623/17.15 |

\* cited by examiner

//  EXPANDABLE CORPECTOMY CAGE

CROSS-REFERENCE TO RELATED APPLICATIONS

This application claims priority under 35 U.S.C. §119 to provisional application Ser. No. 61/448,981 filed Mar. 3, 2011, herein incorporated by reference in its entirety.

FIELD OF THE INVENTION

The invention relates to an expandable corpectomy cage having non-weight bearing telescoping members which are expandable and retractable and a weight-bearing sleeve fit over the telescoping members so that the sleeve bears axial loads when the assembled cage is implanted in a patient.

BACKGROUND OF THE INVENTION

A corpectomy is a surgical procedure wherein a portion of the vertebral body and adjacent intervertebral discs are removed to relieve pressure or decompress the spinal cord and nerves. A corpectomy cage is used to fill the space created by the vertebrae removal. Two types of cages are generally available: A solid fixed height cage and an expandable cage. Fixed cages are manufactured in various heights so that one cage can be selected to best fit the cavity created by the removed vertebral body. Alternatively, an expandable cage having a variable height can be used to maintain spacing of the vertebrae above and below the removed body material. Such expandable cages typically include telescoping members with a physical mechanism to retain the members at the selected height. For example, telescoping members are formed with threaded or ratcheting interconnections, or the use of pins, set screws and the like, to fix the members at a selected height.

Both types of cages have limitations and problems. Fixed or solid cages have excellent structural integrity, but are cumbersome to place. The fixed cage must be exactly the right height. Otherwise, if the cage is too big, it can cause over distraction to the vertebral bodies or damage the vertebral body above and below the cage. If the cage is too small, it can move out of position. Expandable cages are much easier to place and size correctly. However, the mechanical mechanism used to expand the cage may fail in vivo, which can lead to catastrophic results. The telescoping members are weight bearing so as to support the axial loads on the cage when the cage is implanted. Thus, the strength of the case depends upon the inner connection between the telescoping members. If the physiologic load becomes too great, the cage will collapse, thereby causing potentially serious medical problems for the patient. Thus, the structural integrity of an expandable case is less than a fixed or solid cage.

Some commercially available expandable cage are made of metal. These metal cages cause artifact on MRI or CT scans, thereby decreasing the ability to visualize nearby anatomy. Metal cages are also much harder than bone, and can telescope into the vertebral bodies above and below the cage. Commercially available fixed cages are made of other materials, such as carbon fiber, or plastic, which eliminate artifacts on MRI and CT scans.

Accordingly, a primary objective of the present invention is the provision of an improved expandable corpectomy cage which overcomes the problems of the prior art.

Another objective of the present invention is the provision of an expandable corpectomy cage having structural integrity and which is easy to use.

Still another objective of the present invention is the provision of an expandable corpectomy cage which is made of non-metallic materials so as to avoid scanning and imaging artifacts.

Yet another objective of the present invention is the provision of a corpectomy cage having telescoping members which are non-load bearing, and a load-bearing sleeve around the telescoping members.

A further objective of the present invention is the provision of a corpectomy cage having C-shaped telescoping members with aligned openings for receiving bone fusion material, and a sleeve to cover the openings so as to retain the fusion material within the cage.

Still another objective of the present invention is the provision of an improved corpectomy cage having minimal weight and increased strength.

A further objective of the present invention is the provision of an improved corpectomy cage which is economical to manufacture, and safe and durable in use.

These and other objectives will become apparent from the following description of the invention.

SUMMARY OF THE INVENTION

The expandable corpectomy cage of the present invention includes upper and lower telescoping members or segments which are movable axially between extended and retracted positions. Each segment has an internal cavity for receiving bone fusion material. A C-shaped sleeve or cover removably fits over the opening in opposite sides of the telescoping members. The primary function of the sleeve is to support axial loads on the assembly to prevent the telescoping members from retracting or collapsing. The sleeve also encloses the cavity, which is free from obstructions. The sleeve is retained on the telescoping members by a snap fit, fasteners, or other locking means. The assembly may have a substantially square cross-section or a circular cross-section.

BRIEF DESCRIPTION OF THE DRAWINGS

FIGS. 1-14 of the drawings show a first embodiment of the corpectomy cage of the present invention having a square cross-section.

FIG. 2 is a sectional view taken along lines 2-2 of FIG. 1A.

FIG. 3 is an exploded view of the telescoping members and sleeve of the corpectomy cage of the first embodiment.

FIG. 4 is a plan view from one side of the cage.

FIG. 5 is a sectional view taken along lines 5-5 of FIG. 4.

FIG. 6 is a perspective view of a shortened sleeve for the corpectomy cage.

FIG. 10 is an exploded view of an alternative embodiment of the corpectomy cage.

FIG. 11 is a perspective view of a shortened sleeve for the cage of FIG. 10.

FIG. 15 is a perspective view of the round embodiment of the corpectomy cage of the present invention.

FIG. 16 is another perspective view of the round corpectomy cage.

FIG. 17 is an exploded view of the round corpectomy cage.

FIG. 18 is an enlarged view taken along line 18 of FIG. 16.

FIG. 19 is a side elevation view of the round corpectomy cage.

FIG. 20 is a sectional view taken along lines 20-20 of FIG. 19.

FIG. 21 is a sectional view taken along lines 21-21 of FIG. 19.

DETAILED DESCRIPTION OF THE PREFERRED EMBODIMENTS

Figure 1A:
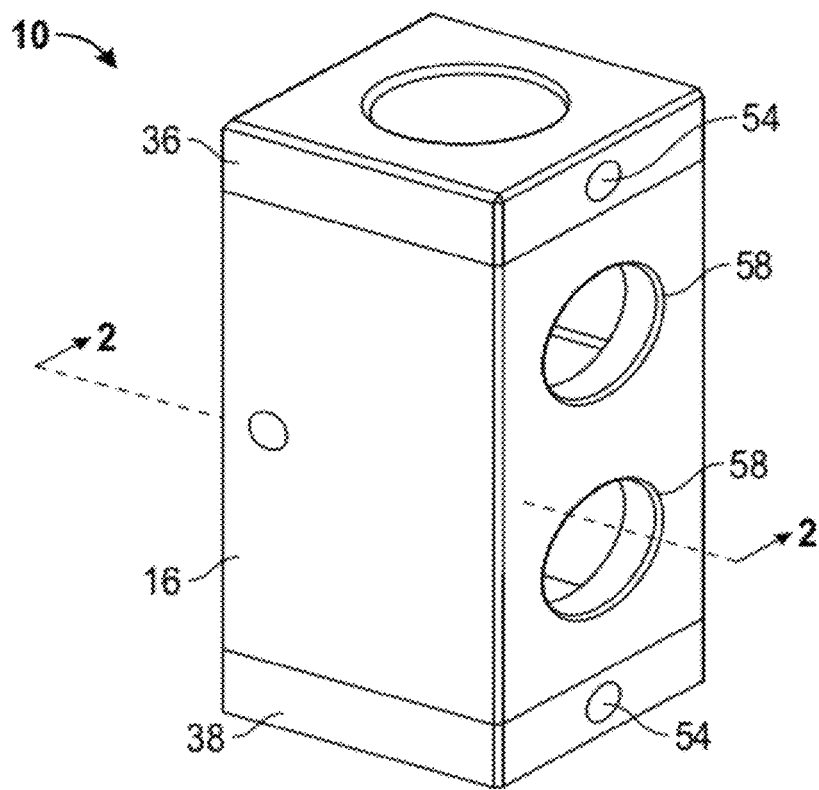
FIG. 1A is a perspective view of the first embodiment of the corpectomy cage according to the present invention.
Figure 1B:
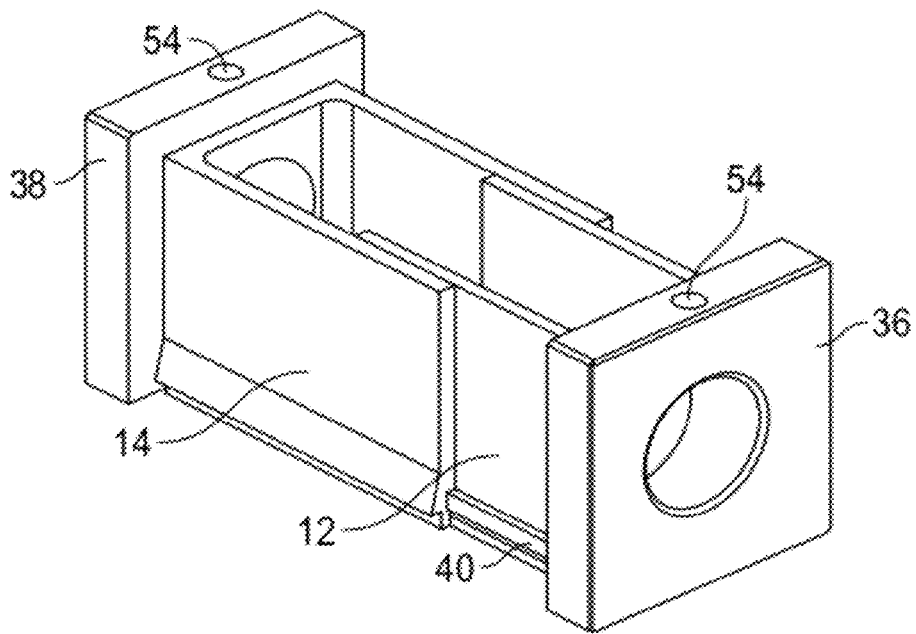
FIG. 1B is a perspective view of the telescoping members of the first embodiment.
Figure 2:
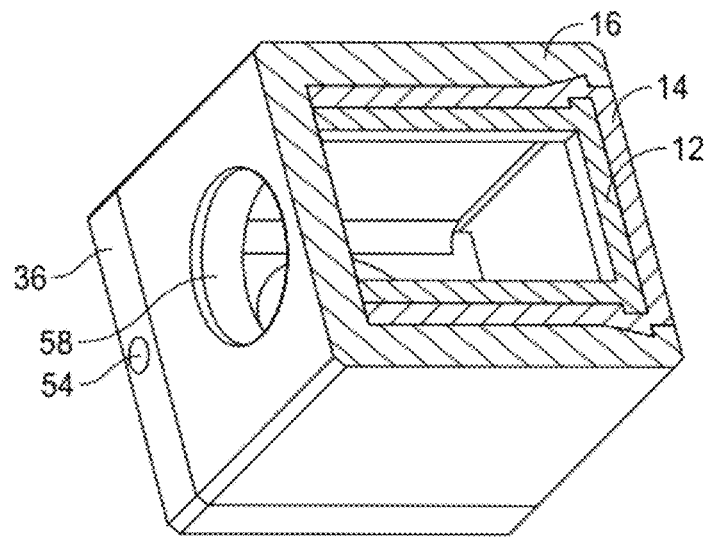

A square embodiment of the corpectomy cage of the present invention is designated by the reference numeral 10 in FIGS. 1-14. FIGS. 15-21 show a round embodiment of the corpectomy cage designated by the reference numeral 10A. The cage 10 has three primary components: an inner telescoping member 12, and outer telescoping member 14 and a sleeve or cover 16. Similarly, the cage 10A has three primary components: an inner telescoping member 12A, an outer telescoping member 14A, and a sleeve or cover 16A. The cages 10 and 10A, and their components, function similarly to one another in implantation and in use.

The inner telescoping member 12 has opposite sides 18 with an inner connecting web or back wall 20, with an opening 22 opposite the web 20. Thus, the inner telescoping member 12 has a general C-shape with squared corners. The outer telescoping member 14 has opposite sides 24, with an inner connecting web or back wall 26, with an opening 28 opposite the web 26. Thus, the outer telescoping member 14 has a C-shape with squared corners. The sidewalls 18 of the member 12 have a narrower spacing than the side walls 24 of the member 14, such that the members 12, 14 can be assembled for axial movement relative to one another.

Figure 3:
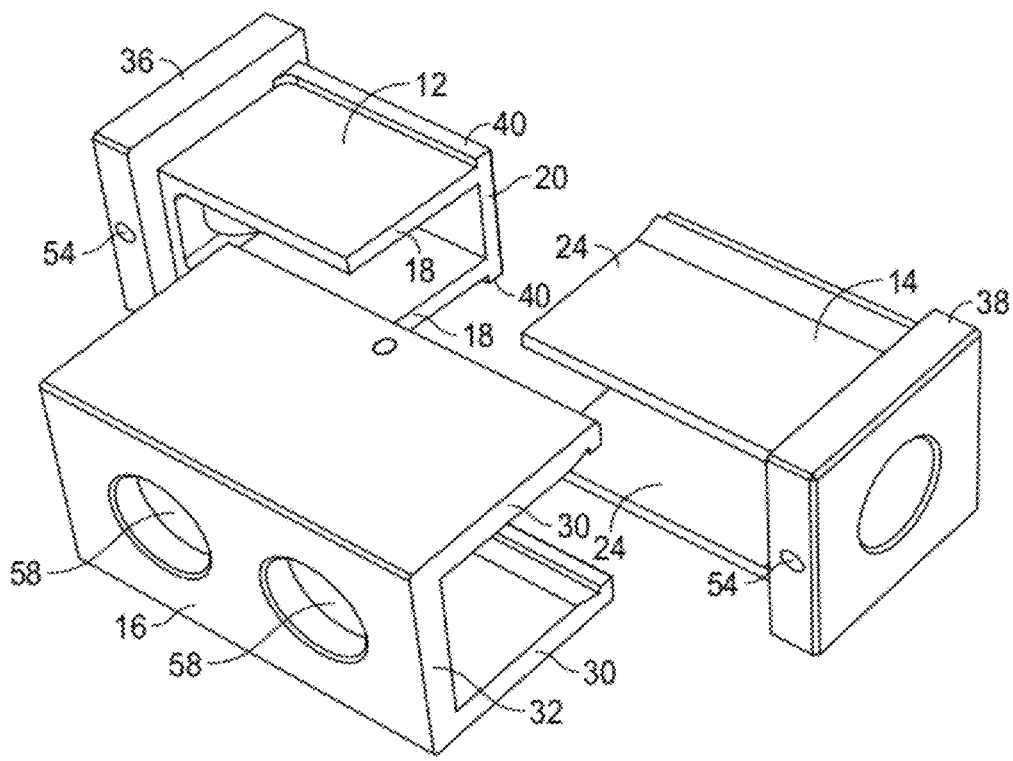
Figure 3A:
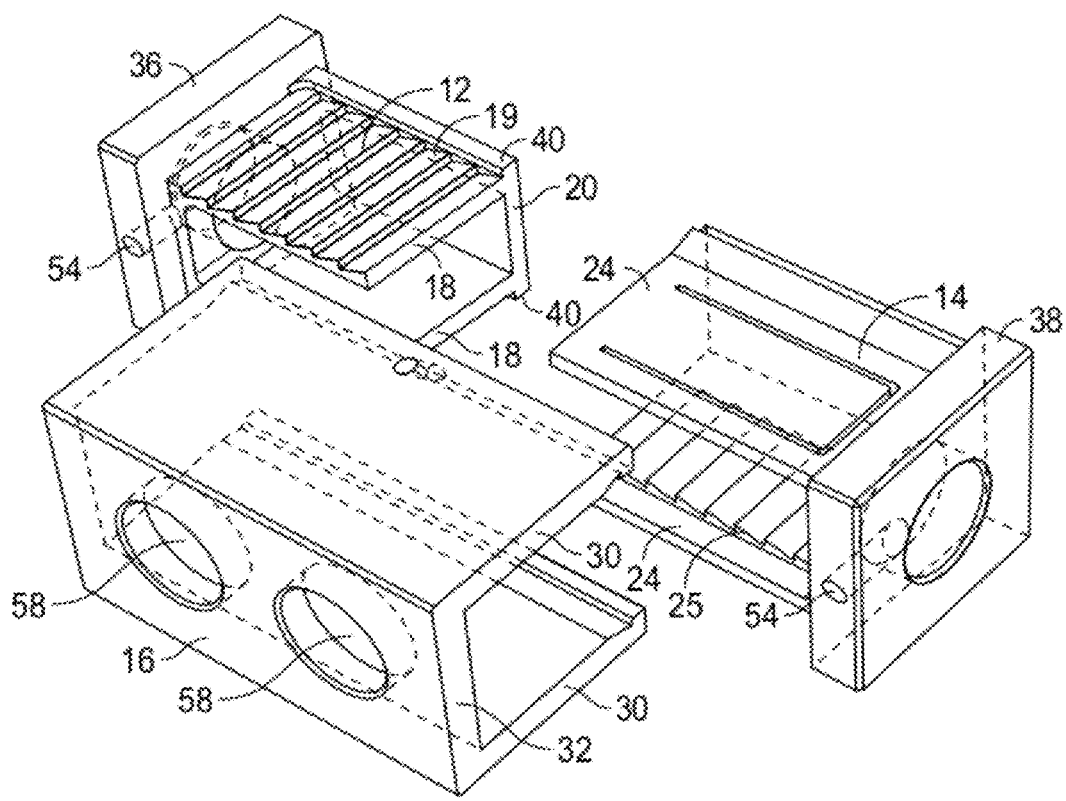
FIG. 3A is an exploded view of an alternate embodiment with ratcheting side walls on the telescoping member.
Figure 4:
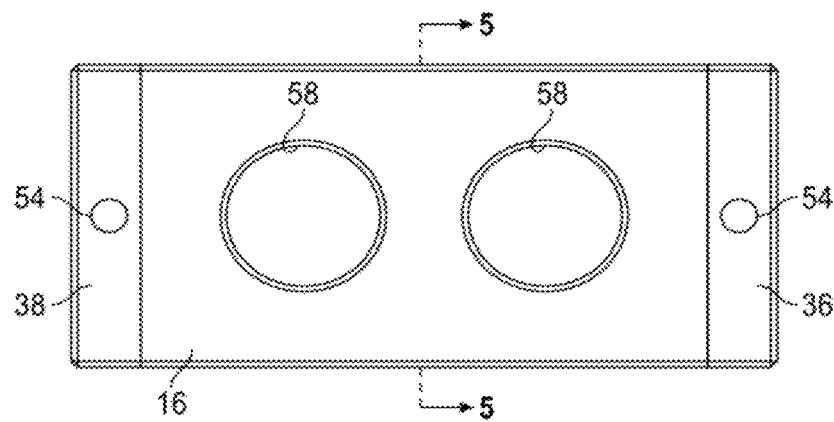
Figure 5:
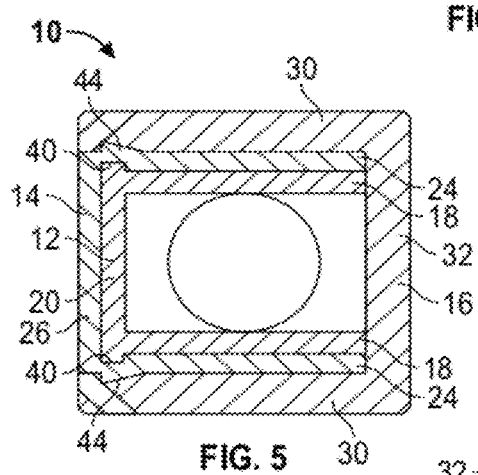

In the alternative embodiment shown in FIG. 3A, the sides 18 have external ratchets 19 and the side 24 have internal ratchets. The ratchets 19, 24 matingly overlap and allow the telescoping members to be extended one step at a time, such as 1 mm increments.

The inner and outer telescoping members 12A, 14A each have cylindrical side walls 18A, 24A, respectively, with enlarged openings therein. The diameter of member 12A is smaller than the diameter of member 14A, so that the members can be assembled for axial movement relative to one another.

The sleeve 16 includes opposite sides 30 with a web or front wall 32 extending between the opposite sides, and an opening 34 opposite the web 32. The sleeve 16 has a C-shaped profile with squared corners. Similarly, the sleeve 16A has opposite sides 30A with an opening 34A.

The inner and outer telescoping members 12, 14 each have an end plate 36, 38, respectively. Similarly, the inner and outer round telescoping members 12A, 14A have respective end plates 36A, 38A.

The inner and outer telescoping members 12, 14 and 12A, 14A are adapted to matingly and slidably fit together in a telescoping manner for axial expansion and retraction. The sleeve 16 is adapted to matingly fit over the outer telescoping member 14A, with the opposite ends of the sleeve 16 engaging the inner surfaces of the end plates 36, 38. Similarly, the sleeve 16A is adapted to matingly fit over the outer telescoping member 14A, with the ends of the sleeve 16A abutting the inner surfaces of the end plates 36A, 38A. This assembly of the inner and outer telescoping members and the sleeve forms the cage 10, 10A with the sleeve 16, 16A being load bearing. Thus, with this cage configuration of the present invention, the sleeves 16, 16A bear the axial loads from the vertebral bodies on the end plates 36, 38 or 36A, 38A. The sleeves 16, 16A thereby preclude or prevent the telescoping members 12, 14 and 12A, 14A from collapsing or retracting in vivo relative to one another. Also, the sleeves 16, 16A eliminate the need for a fastener between the inner and outer telescoping members, as in the prior art, to fix the relative positions of the telescoping members relative to one another. Thus, the telescoping members 12, 14 and 12A, 14A are non-load bearing.

Preferably, the inner and outer telescoping members 12, 14 have overlapping or interlocking structure so that these members slide axially without transverse separation. More particularly, in the preferred embodiment, the inner telescoping member 12 has an external tongue or lip 40 extending outwardly from each side 18. The outer telescoping member has internal grooves 42 on each side 24 to slidably receive the tongues or lips 40 on the inner telescoping member 12. For the round inner and outer telescoping members 12A, 14A, the circular shape controls the sliding axial movement of the members relative to one another.

The sleeve 16 can be retained on the telescoping members 12, 14 in any convenient manner. In a preferred embodiment, the sleeve 16 snap fits onto the outer telescoping member 14. More particularly, the outer telescoping member 14 has an axially extending external projection or bead 44 with a beveled surface and a retention shoulder extending along each side 24. The sleeve 16 has an internal groove 46 along the inside of each side wall 30. The sides 30 of the sleeve are resilient such that the sleeve snap fits over the beads 44, which are matingly received within the grooves 46 of the sleeve 16. Thus, the sleeve 16 is retained on the outer telescoping member 14 by the overlapping beads 44 and grooves 46. The sleeve 16 can be removed from the outer telescoping member 14 by spreading the sides 30 to disengage the beads 44 and grooves 46.

In an alternative embodiment shown in FIGS. 10-14, the sleeve 16 is retained on the telescoping members 12, 14 using screws 48 which extend through the sleeve and into threaded holes in the telescoping members 12, 14. For the round cage 10A, the sides 30A of the sleeve 16A are resilient, such that the sleeve 16A can be snap fit over the telescoping members 12A, 14A.

Figure 6:
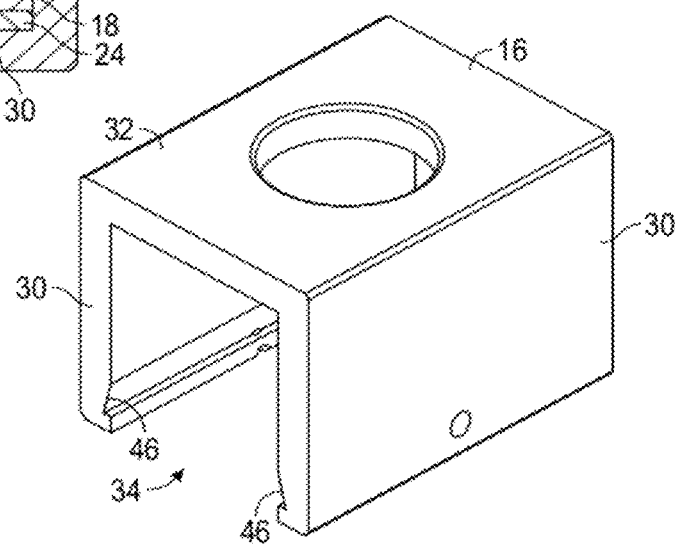
Figure 7A:
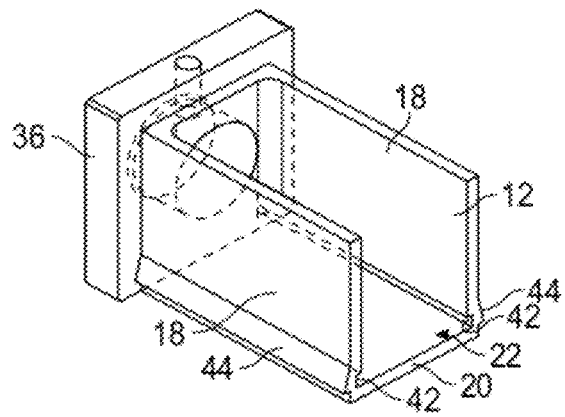
FIG. 7A is a perspective view of the inner telescoping members.
Figure 7B:
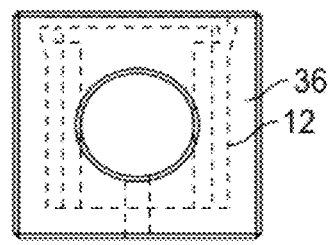
FIG. 7B is an end view of the inner telescoping members shown in FIG. 7A.
Figure 7C:
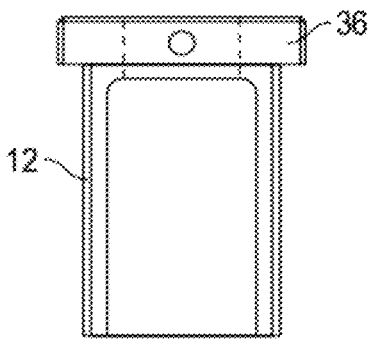
FIG. 7C is an elevation view of one side of the inner telescoping member.
Figure 7D:
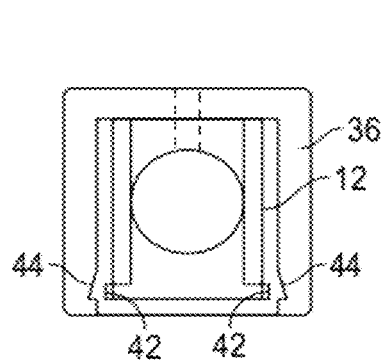
FIG. 7D is an end view from the opposite end of FIG. 7B.
Figure 7E:
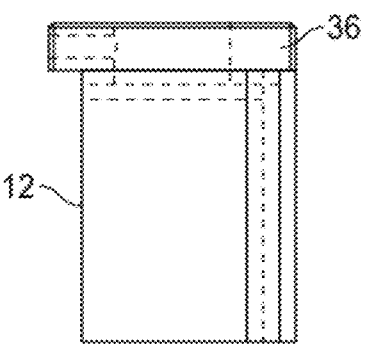
FIG. 7E is another elevation view of the inner telescoping member.
Figure 8A:
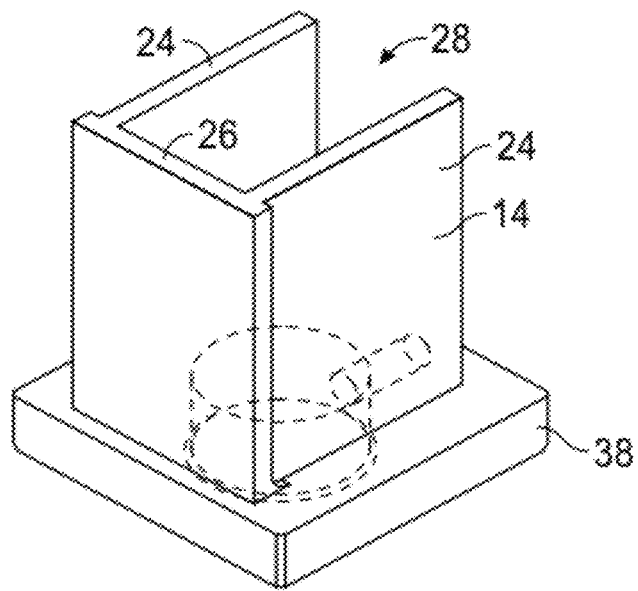
FIG. 8A is a perspective view of the outer telescoping members.
Figure 8B:
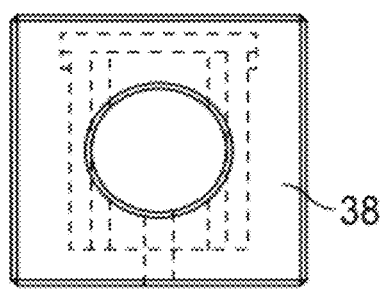
FIG. 8B is an end view of the outer telescoping members shown in FIG. 8A.
Figure 8C:
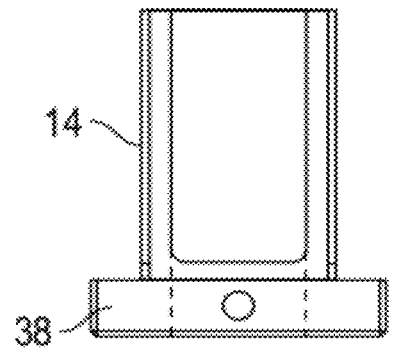
FIG. 8C is an elevation view of one side of the outer telescoping member.
Figure 8D:
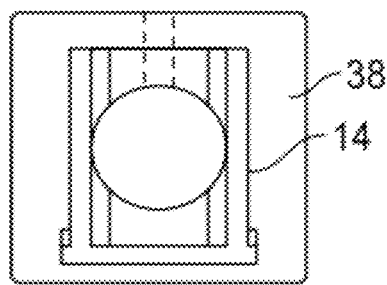
FIG. 8D is an end view from the opposite end of FIG. 8B.
Figure 8E:
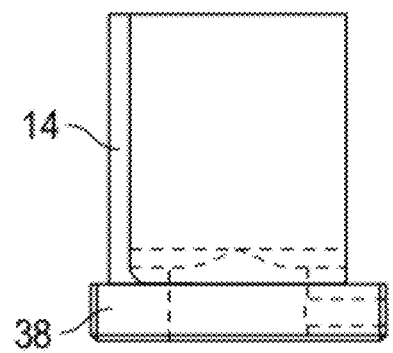
FIG. 8E is another elevation view of the outer telescoping member.
Figure 9A:
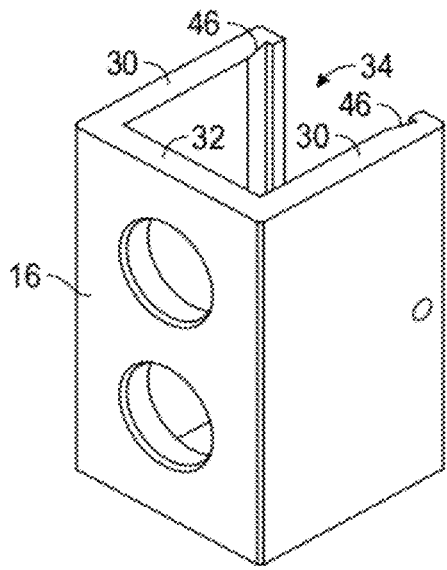
FIG. 9A is a perspective view of the sleeve of the corpectomy cage.
Figure 9B:
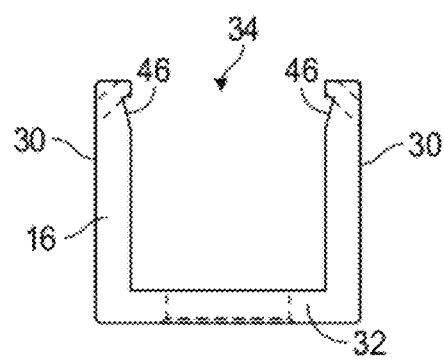
FIG. 9B is a top plan view of the sleeve.
Figure 9C:
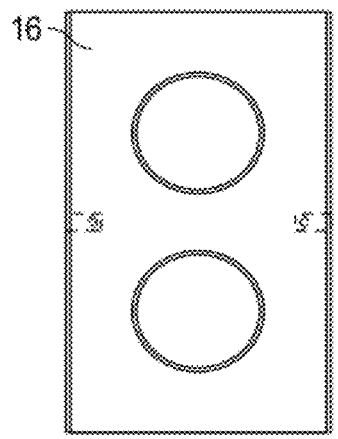
FIG. 9C is an elevation view from one side of the sleeve.
Figure 9D:
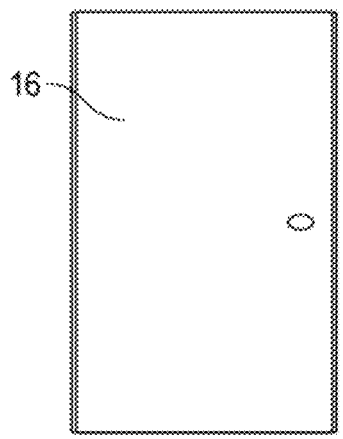
FIG. 9D is an elevation view from another side of the sleeve.
Figure 10:
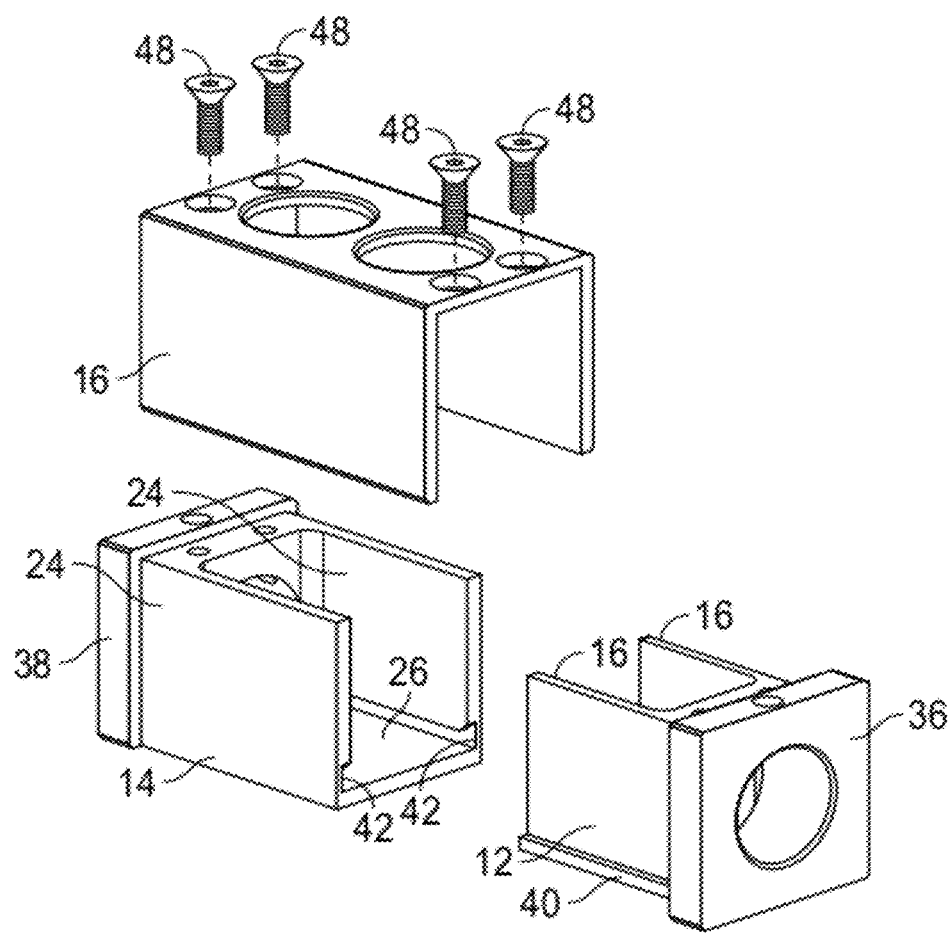
Figure 11:
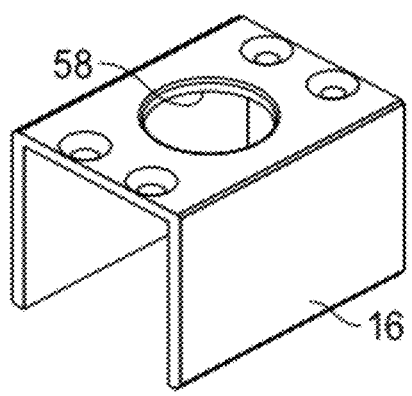
Figure 12A:
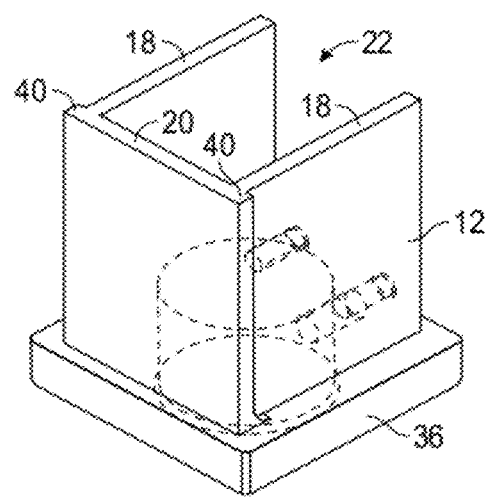
FIG. 12A is a perspective view of the inner telescoping member of the corpectomy cage shown in FIG. 10.
Figure 12B:
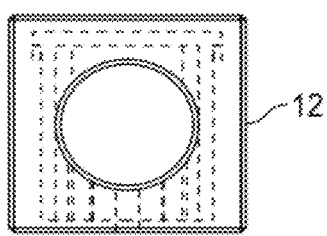
FIG. 12B is an end view of the inner telescoping members shown in FIG. 12A.
Figure 12C:
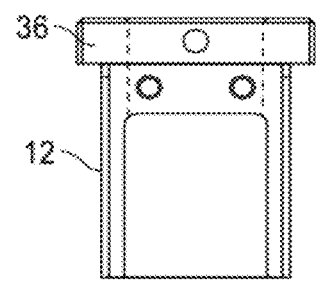
FIG. 12C is an elevation view of one side of the inner telescoping member shown in FIG. 12A.
Figure 12D:
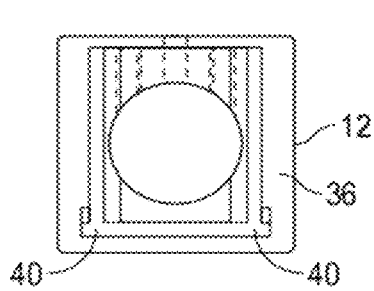
FIG. 12D is an end view from the opposite end of FIG. 12B.
Figure 12E:
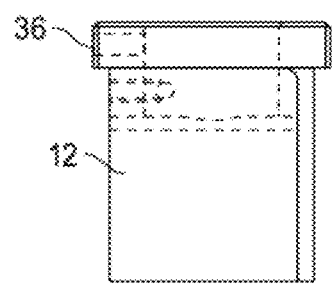
FIG. 12E is another elevation view of the inner telescoping member of FIG. 12A.
Figure 13A:
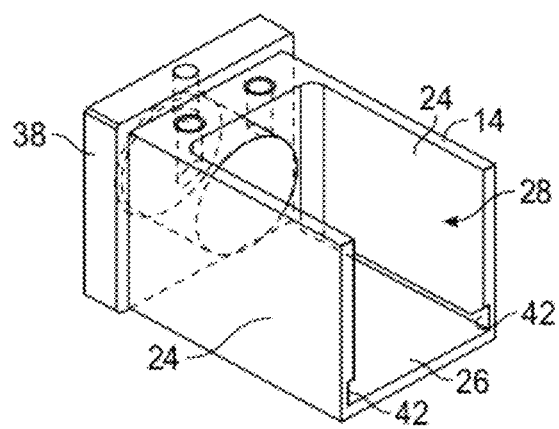
FIG. 13A is a perspective view of the outer telescoping member of the cage shown in FIG. 10.
Figure 13B:
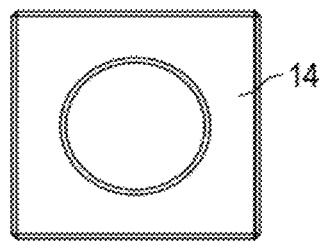
FIG. 13B is an end view of the outer telescoping members shown in FIG. 13A.
Figure 13C:
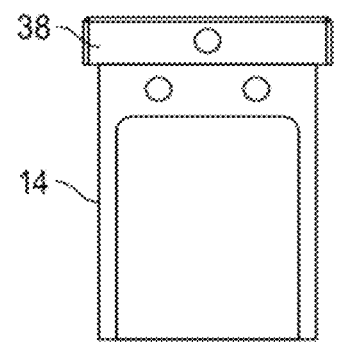
FIG. 13C is an elevation view of one side of the outer telescoping member shown in FIG. 13A.
Figure 13D:
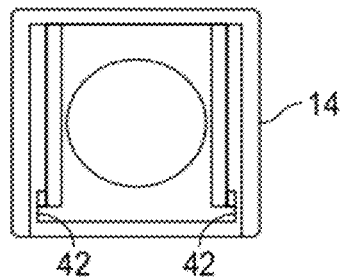
FIG. 13D is an end view from the opposite end of FIG. 13B.
Figure 13E:
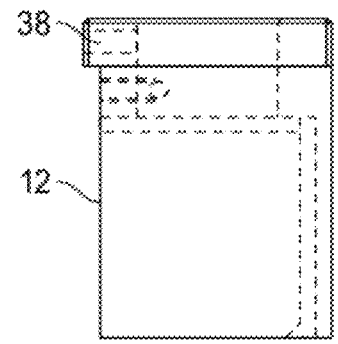
FIG. 13E is another elevation view of the outer telescoping member of FIG. 13A.
Figure 14A:
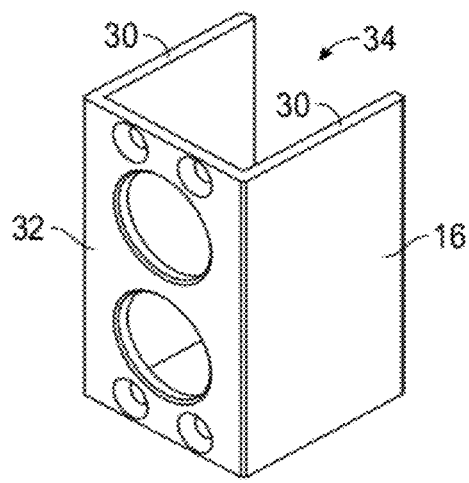
FIG. 14A is a perspective view of the sleeve of the corpectomy cage shown in FIG. 10.
Figure 14B:
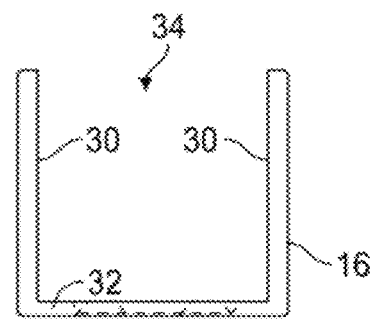
FIG. 14B is a top plan view of the sleeve of FIG. 14A.
Figure 14C:
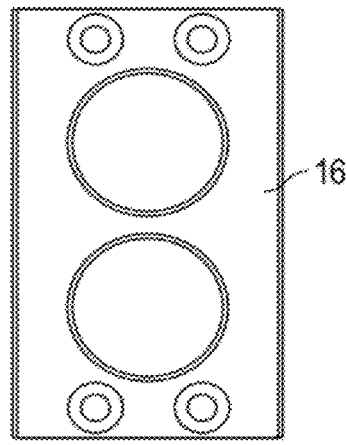
FIG. 14C is an elevation view from one side of the sleeve shown in FIG. 14A.
Figure 14D:
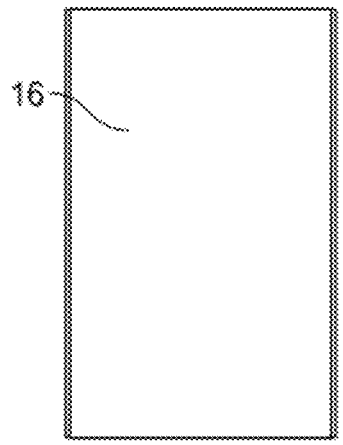
FIG. 14D is an elevation view from another side of the sleeve of FIG. 14A.
Figure 15:
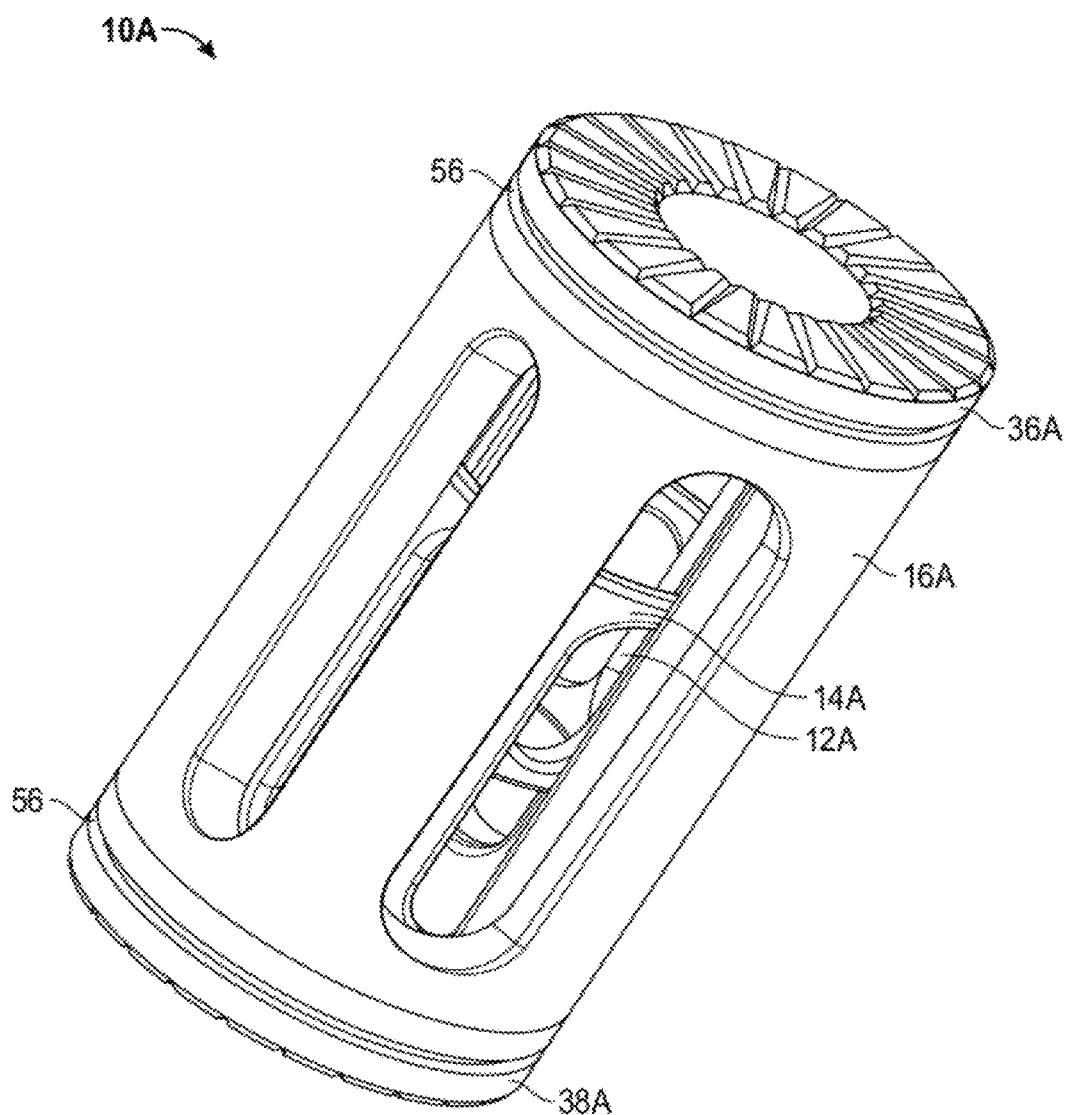
FIGS. 15-21 show a second embodiment of the corpectomy cage of the present invention having a round cross-section.
Figure 17:
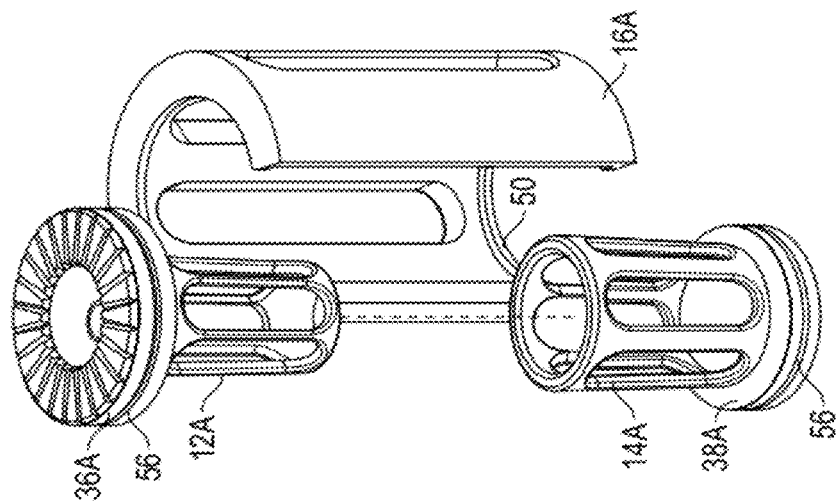
Figure 16:
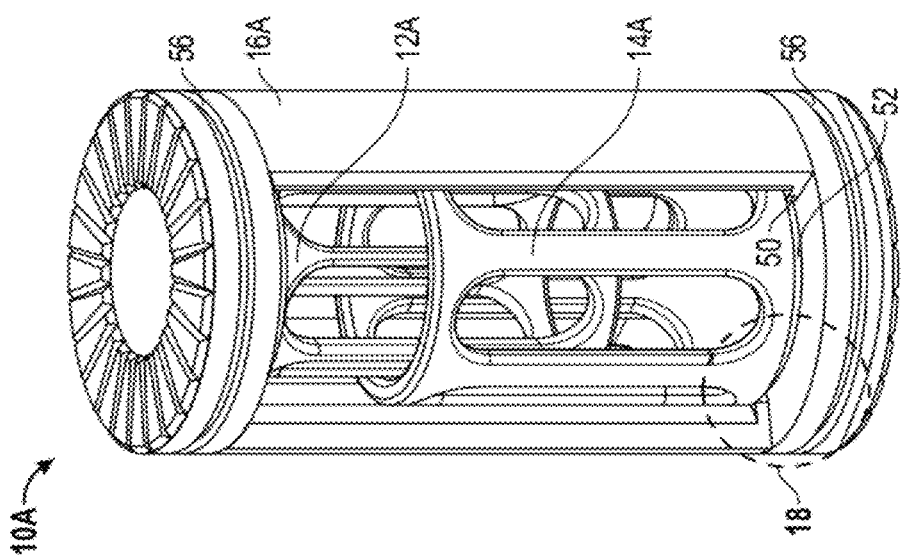
Figure 18:
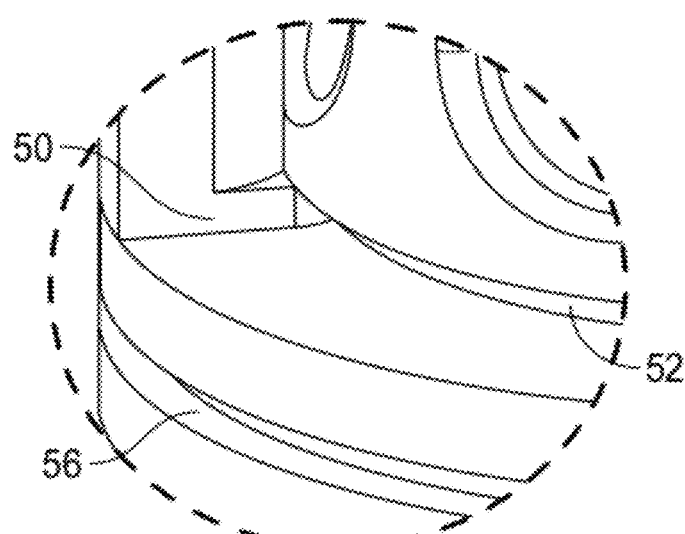
Figure 19:
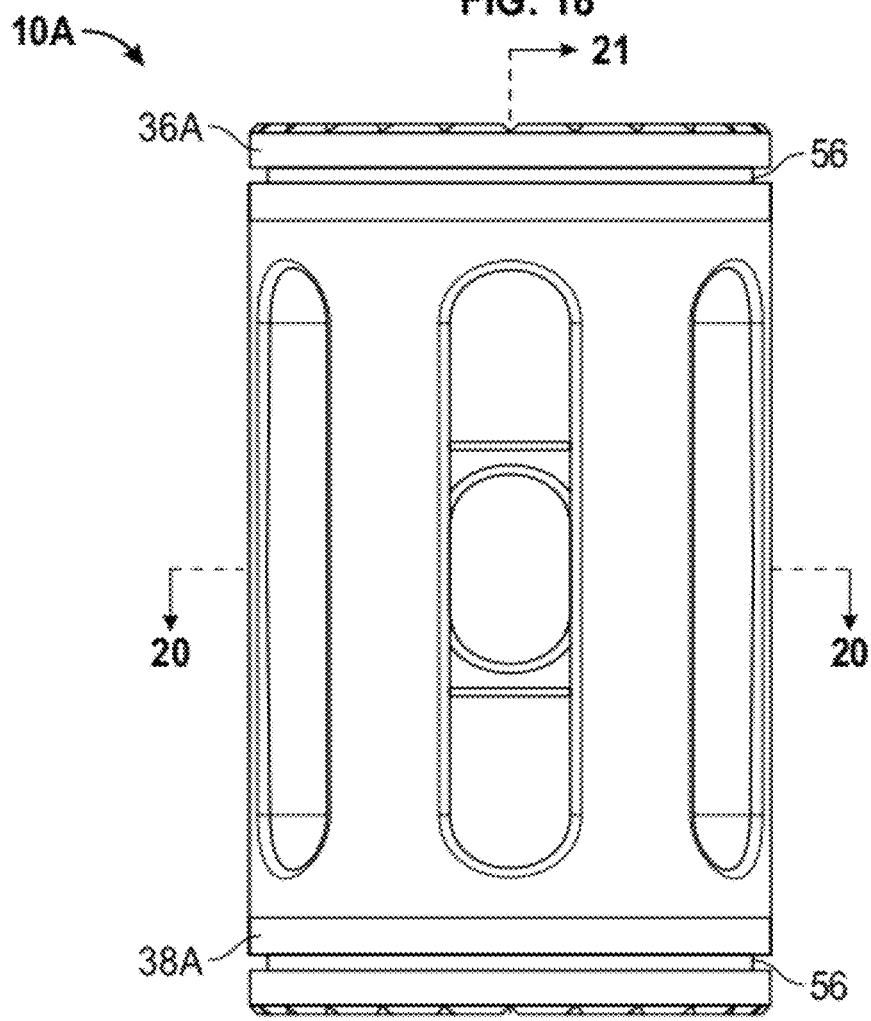
Figure 20:
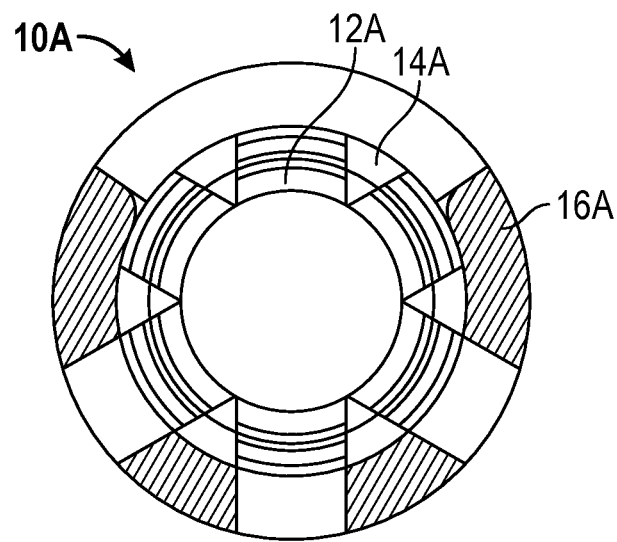
Figure 21:
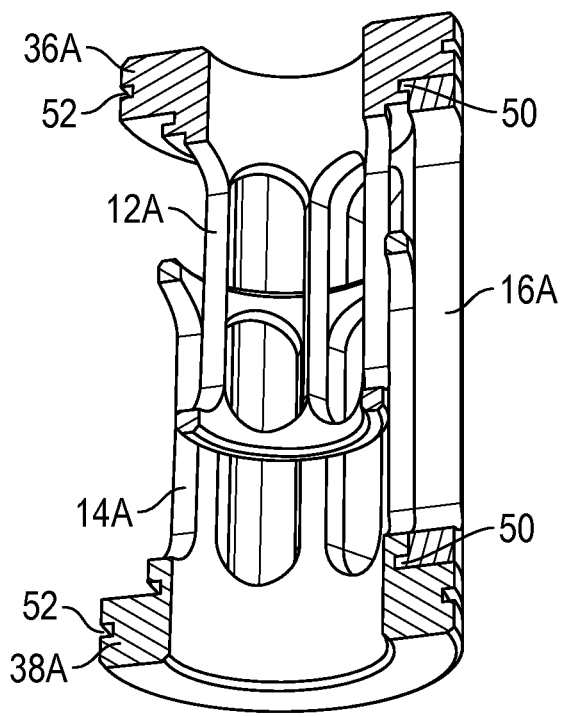

It is understood that the sleeve 16, 16A is generally selected by the surgeon performing the corpectomy from a set of sleeves having various heights or lengths, such that the assembled cage 10, 10A will properly fit between the upper and lower vertebral bodies. For example, FIGS. 1-4 show a longer or taller sleeve 16, while FIG. 6 shows a shorter sleeve. Similarly, FIG. 11 shows a shorter sleeve compared to the longer sleeve shown in FIG. 14A.

While the sleeve 16, 16A prevents the telescoping members 12, 14 and 12A, 14A from being retracted toward one another, in another alternative embodiment, the sleeve can prevent extension of the telescoping members relative to one another. For example, in the round cage 10A shown in FIGS. 15-21, the sleeve 16A has a radially directed lip 50 extending inwardly from each end for receipt in a groove 42 on each telescoping member 12A, 14A. The lips 50 of the sleeve 16A are received in the grooves 52 of the telescoping members 12A, 14A to prevent the members from expanding axially.

The cages 10, 10A of the present invention are implanted using conventional methodology. For example, the tips of a hand held expanding tool are received in holes 54 in the end plates 36, 38 of the telescoping members 12, 14, or in a perimeter groove 56 in the end plates 36A, 38A of the telescoping members 12A, 14A. After the telescoping members 12, 14, 12A, 14A, are implanted and bone fusion material is added to the cage cavity, the sleeve 16, 16A is placed over the telescoping members so as to fix the height of the cage 10, 10A. The axial loads on the cage 10, 10A are then born by the sleeve 16, 16A, rather than by the telescoping members 12, 14 and 12A, 14A. The cages 10, 10A have enlarged fusion openings 58, 58A to accommodate bone growth around and through the cage. The center cavity of the cage is substantially unobstructed for improved or enhanced bone growth and fusion.

Since the sleeve 16, 16A has a fixed length so as to be load bearing, the telescoping segments 12, 14 and 12A, 14A, as well as the sleeves 16, 16A, can be made of non-metallic material which does not interfere or otherwise produce artifacts when scanned or imaged. Thus, the cages 10, 10A can be made of any high strength, lightweight, biocompatible material.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A corpectomy cage, comprising:
   an inner member having a cylindrical sidewall, a first end and a second end opposite the first end, the cylindrical sidewall having a circumferential groove;
   an outer member having a cylindrical sidewall, a first end and a second end opposite the first end, the cylindrical sidewall having a circumferential groove, wherein the cylindrical side wall and the second end of the inner member is at least partially disposed within the cylindrical side wall and the second end of the outer member in a telescoping, non-load bearing engagement to allow axial movement between extendable and retractable positions, wherein the first end of the inner member is located opposite to the first end of the outer member; and
   a cylindrical sleeve configured to bear axial loads on the cage and having a fixed length, a first end, a second end, a first lip extending radially inward proximate the first end of the sleeve, and a second lip extending radially inward proximate the second end of the sleeve, the sleeve fit over the outer member with the first lip engaging the circumferential groove on the inner member and the second lip engaging the circumferential groove on the outer member.

2. The corpectomy cage of claim 1 wherein the sleeve is snap fit onto the outer member.

3. The corpectomy cage of claim 1 wherein the sleeve comprises resilient sidewalls such that the sleeve can be snap fit over the inner and outer members.

4. The corpectomy cage of claim 1 wherein the inner member, outer member, and sleeve have a substantially round cross-section when assembled.

5. The corpectomy cage of claim 1 wherein the sleeve has an axial opening for receiving the inner member and outer member.

6. The corpectomy cage of claim 1 wherein the sleeve is selected from a set of sleeves each having a different length.

7. The corpectomy cage of claim 1 wherein the inner member and the outer member have a circular profile, and the sleeve has a C-shaped profile.

8. The corpectomy cage of claim 1 wherein the inner member comprises an end plate disposed at the first end thereof, the outer member comprises an end plate disposed at the first end thereof.

9. The corpectomy cage of claim 8 wherein each of the end plates comprises a perimeter groove configured to be engaged by a tool.

10. A corpectomy cage for use between a first vertebra and a second vertebra in place of removed intervertebral discs and at last a portion of a vertebral body of a third vertebra located between the first vertebra and the second vertebra, the corpectomy cage comprising:
   a first segment with a cylindrical sidewall, a circumferential groove, and an end plate, the end plate configured to engage the first vertebra;
   a second segment with a cylindrical sidewall, a circumferential groove, and an end plate, the end plate configured to engage the second vertebra;
   a C-shaped cover with a fixed length, the cover having a first radial lip and a second radial lip extending inwardly and spaced apart from the first radial lip;
   the first and second segments being slidably assembled; and the cover removably mounted over the assembled first and second segments between the end plates so as to support physiologic loads on the cage, wherein the first radial lip engages the circumferential groove on the first segment and the second radial lip engages the circumferential groove on the second segment.

11. The corpectomy cage of claim 10 wherein the cover is snap fit onto one of the segments.

12. The corpectomy cage of claim 10 wherein the cover has resilient side walls.

13. The corpectomy cage of claim 10 wherein the cover is selected from a set of covers each having a different length.

14. The corpectomy cage of claim 10 wherein the assembled first and second segments have an adjustable length.

15. The corpectomy cage of claim 14 wherein the first and second segments are free from mechanical fasteners connecting the segments together.

16. The corpectomy cage of claim 10 wherein the cover is load bearing and the first and second segments are non-load bearing.

17. The corpectomy cage of claim 10 wherein the cage has an unobstructed internal cavity.

\* \* \* \* \*